United States Patent
Schmelzeisen-Redeker et al.

(10) Patent No.: US 8,439,834 B2
(45) Date of Patent: May 14, 2013

(54) ANALYSIS SYSTEM WITH USER-FRIENDLY DISPLAY ELEMENT

(75) Inventors: Guenther Schmelzeisen-Redeker, Lorsch (DE); Wolfgang Heck, Ladenburg (DE); Stefan Kalveram, Viernheim (DE); Andreas Menke, Mannheim (DE); Wilfried Schmid, Mannheim (DE); Friedrich Ziegler, Stuttgart (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1385 days.

(21) Appl. No.: 12/129,050

(22) Filed: May 29, 2008

(65) Prior Publication Data

US 2009/0012374 A1    Jan. 8, 2009

Related U.S. Application Data

(63) Continuation of application No. PCT/EP2006/069229, filed on Dec. 1, 2006.

(30) Foreign Application Priority Data

Dec. 2, 2005 (EP) .................................. 05026289

(51) Int. Cl.
*A61B 5/00* (2006.01)
*G01N 33/48* (2006.01)
*H01L 29/15* (2006.01)
*H01L 31/04* (2006.01)

(52) U.S. Cl.
USPC .............. 600/301; 422/50; 422/68.1; 257/53; 257/59; 257/72

(58) Field of Classification Search ........................ None
See application file for complete search history.

(56) References Cited

U.S. PATENT DOCUMENTS

| | | | | |
|---|---|---|---|---|
| 4,106,951 A | * | 8/1978 | Masi | 136/263 |
| 5,041,952 A | * | 8/1991 | Janda et al. | 362/183 |
| 5,286,362 A | | 2/1994 | Hoenes et al. | |
| 6,144,162 A | | 11/2000 | Smith | |
| 6,197,418 B1 | * | 3/2001 | Cloots et al. | 428/332 |
| 6,579,237 B1 | | 6/2003 | Knoblich | |
| 7,595,726 B2 | * | 9/2009 | Nissels et al. | 340/539.29 |
| 7,713,240 B2 | * | 5/2010 | Istoc et al. | 604/131 |
| 2002/0180721 A1 | | 12/2002 | Kimura et al. | |
| 2003/0004403 A1 | | 1/2003 | Drinan et al. | |
| 2003/0035109 A1 | | 2/2003 | Hartwich et al. | |
| 2003/0217966 A1 | * | 11/2003 | Tapsak et al. | 210/500.21 |
| 2004/0032382 A1 | * | 2/2004 | Cok et al. | 345/82 |
| 2004/0135749 A1 | * | 7/2004 | Kondakov et al. | 345/82 |
| 2004/0258866 A1 | | 12/2004 | Shiba et al. | |
| 2005/0007392 A1 | * | 1/2005 | Kasai et al. | 345/690 |
| 2005/0015115 A1 | | 1/2005 | Sullivan et al. | |
| 2005/0113655 A1 | | 5/2005 | Hull | |
| 2005/0143671 A1 | | 6/2005 | Hastings et al. | |
| 2005/0187444 A1 | * | 8/2005 | Hubner et al. | 600/322 |
| 2006/0098203 A1 | | 5/2006 | Kalveram | |
| 2006/0121625 A1 | | 6/2006 | Clemens et al. | |
| 2006/0125736 A1 | * | 6/2006 | Lee | 345/76 |

FOREIGN PATENT DOCUMENTS

| | | |
|---|---|---|
| CA | 2050677 | 3/1992 |
| DE | 10253154 A1 | 5/2004 |
| DE | 10341093 A1 | 4/2005 |
| DE | 202005012358 U1 | 11/2005 |
| JP | 4142785 * | 5/1992 |
| WO | 2004048881 A2 | 6/2004 |
| WO | WO2005/089834 * | 9/2005 |

OTHER PUBLICATIONS

Klein et al (Lancet, 1997, vol. 350, pp. 197-204).*
Salditt (SMTA News and Journal of Surface Mount Technology, 2004, vol. 17, pp. 19-24).*
Espacenet English abstract for JP4142785, downloaded from the Web Jul. 23, 2012.*
Lo et al (International Workshop on Body Sensor Networks, 2005, pp. 1-5).*

* cited by examiner

*Primary Examiner* — Karen Canella
(74) *Attorney, Agent, or Firm* — Krieg DeVault LLP

(57) ABSTRACT

A portable medical system is provided for the purposes of analysis and/or medication, the system having at least one of a medical monitoring device, an analysis device and a medication device. The portable medical system comprises at least one display element comprising at least one organic light-emitting diode display. An optimization device can be provided that comprises a brightness sensor and is configured to optimize the brightness, contrast and/or power consumption of the at least one display element. Furthermore, a monitoring device can be provided which monitors the functionality of the display element. Faults in the display element can be detected in this way, and a corresponding warning can be output to a person using the portable medical system.

17 Claims, 1 Drawing Sheet

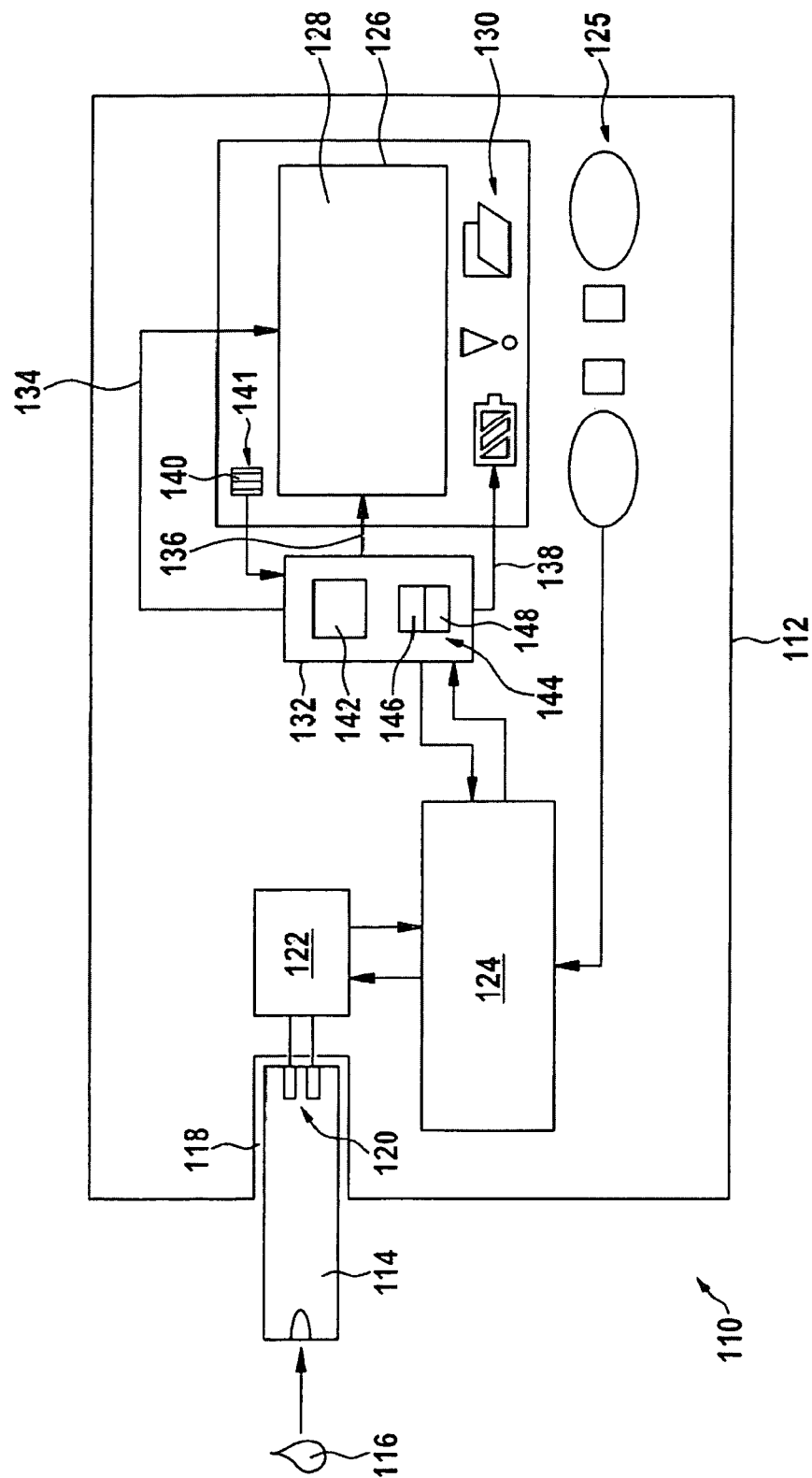

ANALYSIS SYSTEM WITH USER-FRIENDLY DISPLAY ELEMENT

CLAIM OF PRIORITY

The present application is a continuation based on and claiming priority to PCT/EP20061069229, filed Dec. 1, 2006, which further claims the benefit of EP 05 026 289.8, filed Dec. 2, 2005, both of which are hereby incorporated by reference in their entireties.

TECHNICAL FIELD OF THE INVENTION

The present application relates to a portable medical system, and more particularly to a portable medical system for the purposes of analysis and/or medication in the context of homecare systems, e.g. for monitoring blood glucose or for self-medication, for example by means of insulin pumps.

BACKGROUND

Determination of blood glucose concentrations and corresponding medication are an essential part of the daily routine of diabetics. The blood glucose concentration has to be determined quickly and simply several times a day (typically two to seven times) in order, if appropriate, to be able to take suitable medical measures. In many cases, medication is administered by means of automated systems, in particular by what are called insulin pumps.

So as not to restrict the diabetic's daily routine any more than is necessary, suitable portable devices are often employed which are intended to be easy to carry around and to operate, such that the blood glucose concentration can easily be measured, for example, at the workplace or even during leisure time. Various portable devices are presently available on the market, some of them functioning with different measurement techniques and using different diagnostic techniques. A first measurement method is based, for example, on an electrochemical measurement technique, in which a blood sample is applied to an electrode coated with enzymes and mediators. Corresponding test strips for electrochemical measurement methods of this kind are described in U.S. Pat. No. 5,286,362, for example. Other known measurement techniques use optical measurement methods which, for example, are based on the fact that the substance to be detected can react with specific detection reagents, such that there is a change in the color of the reaction mixture. Systems for detecting color reactions of this kind, and therefore for detecting the corresponding analytes, are known from CA 2,050,677, for example.

It has been found that, because of the generally increasing incidence of disease with age, diabetes frequently occurs in elderly people. In elderly people, however, visual acuity is often impaired, particularly in poor lighting. Moreover, damage to the eyes is a common sequela of diabetes mellitus. For this reason, diabetics in particular require easy-to-read display elements in the portable measurement appliances used for self-monitoring. Similar problems also arise in other types of diseases for which portable appliances are used in the context of a homecare concept.

However, the portable medical systems presently available on the market, in particular portable glucose meters, typically use liquid-crystal displays (LCDs) as display instruments for glucose measurement values, warnings, messages, dates, times, etc. Segmented LCDs and also so-called matrix LCDs are used. Because of their low costs and easier control, segmented LCDs are predominantly used. Matrix LCDs are contained in a small number of glucose meters, these meters often being high-quality meters with extensive data management functions.

However, liquid-crystal displays have a number of disadvantages as far as their readability is concerned. In particular, liquid-crystal displays are not self-lighting. Instead, the liquid-crystal elements act only as "switches" for switching local transparency on and off. The symbols presented are thus made visible by means of transmitted light being blocked or let through at certain points of the display or in certain areas of the display. The light has to be provided, however, by means other that the liquid-crystal display itself. On the one hand, this can be done by ambient light being reflected on a reflecting surface behind the liquid-crystal display and being transmitted through the liquid-crystal display. In this case, however, the readability of the liquid-crystal display is strongly dependent on the illuminating strength of the ambient light. In dark surroundings, or in surroundings with poor lighting, liquid-crystal displays can be read only with difficulty or cannot be read at all.

This dependency of the liquid-crystal displays on ambient light can be reduced if light is transmitted through the liquid-crystal displays from behind or from the side (for example by means of light-emitting films or light-emitting diodes) (backlight display). However, a disadvantage of this technique is that the contrast of the display is impaired under good lighting conditions. This contrast cannot be optimized simultaneously for a presentation with and without backlighting, for which reason use of backlighting always leads to a compromise in the contrast of the display element. In addition, backlighting uses up quite a large amount of electrical energy, which can lead to a reduced useful life of the batteries in the meter. This reduced useful life is especially disadvantageous in portable meters in particular, for example portable glucose meters.

A further disadvantage of using liquid-crystal displays is that the readability of the liquid-crystal display is greatly dependent on the reading angle (typically defined as the angle between a normal to the display element and the viewing direction of an observer). This effect occurs both with and without additional backlighting. This greatly restricts the freedom of use of the glucose meter by the diabetic patient. This is particularly disadvantageous in view of the fact that many diabetics use the glucose meter by placing it on a table top in order to carry out a measurement. In some situations, this can involve reading angles at which the display is made difficult or even impossible to read.

In addition to liquid-crystal displays, a number of other display techniques are known. Thus, the technique of organic light-emitting diodes (OLEDs), which is used in various technical modifications, is known from other areas of technology. In organic light-emitting diodes, thin organic layers (one or more organic layers with a total thickness of typically between 50 and 300 nm) are embedded between two electrodes. If an electrical current is passed through the organic layers, a recombination of "electrons" and "holes" (or their organic pendants) takes place in the organic layers, in a manner similar to inorganic semiconductors. Photons are emitted in this recombination. This effect is referred to as organic electroluminescence.

Organic light-emitting diodes are normally constructed as thin-layer systems on a transparent substrate, for example a glass or plastic substrate. Electrode layers and organic layers are usually built up in succession, until the above-described sandwich structure is obtained. A transparent electrode layer, for example indium tin oxide, is normally used as the first electrode layer (for example anode layer). A metal layer, for example calcium or magnesium, is used for example as counterelectrode (usually cathode). The sandwich structure is then suitably encapsulated, in order to protect the structure against the influence of air humidity and oxygen. In addition to this standard structure as described, other structures are also known, for example structures with several OLEDs stacked on one another, or structures in which light is emitted not through the glass substrate, but through a transparent metal electrode layer. Furthermore, there are also various techniques that differ in terms of the organic materials used. Thus, there are techniques in which the materials are composed of (generally vapor-deposited) monomolecular substances. Other techniques use polymers, generally applied by wet chemistry, as organic materials. Hybrid techniques are also known to persons skilled in the art.

Organic light-emitting diodes are now used as lighting means or otherwise for lighting purposes in various technological fields. Examples are cell phones, mixing desks in the audio sector, digital camera displays, and MP3 players or multimedia players. Examples of use are also found in the medical field. In addition to their use as lighting means, applications of OLEDs as display elements are also known in medicine. The medical systems known from the prior art and using OLED displays are typically stationary systems of considerable size, which cannot easily be carried around by a patient on his or her body. Exemplary disclosures of OLEDs for these various purposes and various fields include WO 2004/048881 A2, US 2003/0035109 A1, US 2005/0015115 A1, U.S. Pat. No. 6,579,237 B1, DE 102 53 154 A1, and US 2003/0004403 A1, the disclosures of each of which are hereby incorporated herein by reference in their respective entireties.

It is further known from the prior art to provide a measuring device for determination of an analyte in a liquid sample, comprising a test element with a test field and a detector, in which electrical components are used that are based at least partially on polymer electronics. However, the disadvantage of such measurement devices based on polymer electronics is that polymer electronics, in particular transistors on an organic basis, according to the prior art are still rather susceptible to failure and permit only designs with comparatively low electronic functionality.

A problem in using OLED displays, which is known from other technical fields, is that the displays used often have quite a short useful life and tend to be highly susceptible to errors. This is due in particular to the fact that the organic materials used degrade with time. Furthermore, quality control often proves difficult, and, for example, the electrode materials used (for example reactive metals such as calcium or magnesium) tend to cause oxidization effects. These effects have the result that individual pixels, individual rows or columns, and in some cases entire displays, fail slowly or unexpectedly suddenly. Devices using such displays are generally unable to detect and react to such minimal effects of the kind that arise, for example, through failure of individual rows or columns.

However, specifically in the case of medical appliances, in particular medical appliances used privately for self-monitoring and/or for self-medication, such a failure is often associated with fatal consequences. It can happen, for example, that elderly patients in particular do not notice that faults have occurred or, even if the faults are in fact noticed, they do not react to these faults as they should. This can lead, for example, to incorrect medication, with well-known serious consequences. In this context, so-called segmented displays, for example 7-segment displays, have proven disadvantageous in particular, because in this case the unobserved failure of individual segments can easily lead to distortion of the values displayed. For example, the display "7" can easily result in the display "1" if the top horizontal stroke is missing. In the medical field, a defect of this kind in displays can have fatal consequences.

It is therefore an object of the present invention to make available a portable medical system which is extremely user-friendly in respect of the display properties described above and which is extremely reliable, while at the same time substantially or completely avoiding the described disadvantages of the prior art. Any faults that occur are intended to be identified as quickly as possible, so as to allow appropriate measures to be taken.

SUMMARY

This object and others that will be appreciated by a person of ordinary skill in the art have been achieved according to the embodiments of the present invention disclosed herein. In one embodiment, the present invention comprises a portable medical system which can be used in particular for the purposes of analysis and/or medication. "Portable" is to be understood here as meaning generally that the medical system can be carried around by the patient as part of a homecare system, for example in order to ensure basic medical treatment at home, at work or during leisure activities. For this purpose, in one embodiment the portable medical system is relatively small, for example, with dimensions similar to the dimensions of a typical cell phone. In other embodiment, the system has minimal susceptibility to disturbances such as mechanical vibrations and/or moisture.

One embodiment of the present invention relates to a medical system comprising an analysis system for detecting at least one analyte in a sample. Systems of this kind can, for example, comprise the above-described systems based on corresponding test strips and on devices for evaluating such test strips. In particular, these can be devices for detecting blood glucose and/or cholesterol and/or a coagulation. Other analytes too can be detected, for example a lactate content. In particular, the analysis system can, as has been described above, use at least one reagent that reacts with the analyte to be detected and in so doing triggers an electrochemical change in the reaction mixture and/or a color reaction.

In another embodiment, the medical system can alternatively or additionally comprise a medication device, in particular a medication delivery system such as a pump. This can in particular be an insulin pump for self-medication with insulin, for example an insulin pump which delivers a predefined dose of insulin at regular intervals or which sets a dose according to an input signal. Alternatively or in addition to an analysis device or medication device, the portable medical system can also have another type of medical monitoring device, for example an artificial pancreas and/or a system for continuous monitoring. Devices of this kind are known in different forms to persons skilled in the art and as such are considered part of this disclosure and not explained in any more detail below.

A basic concept of the present invention is that the portable medical system has at least one display element, which comprises at least one organic light-emitting diode display. This can in particular entail a matrix display, for example an organic passive-matrix display. In contrast to segmented displays, for example, matrix displays do not have the above-described disadvantages of faults often being identified only with difficulty. In matrix displays, faults and defects typically occur as (usually harmless) point defects or as easily identifiable row and/or column defects. The possibility of a false reading is therefore greatly reduced.

In addition to the at least one display element, other display elements using different technologies can also be used, for example liquid-crystal displays or inorganic light-emitting diode displays.

In principle, all the OLED techniques known from the prior art, in particular the ones described above, can be used for the organic light-emitting diode displays. In particular, OLEDs can be used that are based on monomolecular organic substances, and displays that comprise polymers. Hybrid technologies are also conceivable. Furthermore, it is not just matrix displays that can be used, but also, for example, segmented displays, for example 7-segment displays, or simple display symbols, for example displays with battery status indications or warnings. Active-matrix displays are also possible in principle, although in this case the costs are increased (which is an acceptable disadvantage, however, especially in the case of high-quality devices).

The advantages of using organic light-emitting diode displays over conventional liquid-crystal displays are many. In particular, much higher contrast can be achieved, as a result of which the readability is considerably improved, even with small character sizes. A further advantage is that organic light-emitting diode displays are self-lighting display elements, which can be easily read even in the dark or in poor lighting. It is possible to dispense with backlighting, which greatly reduces the power consumption compared to conventional liquid-crystal displays. This means that the batteries have much longer useful lives, which is advantageous especially in glucose meters that have motors and other "energy guzzlers".

Another considerable advantage of using organic light-emitting diode displays over conventional LCDs lies in the wide reading angle that is possible. Thus, the reading angle covers an area of almost 180° (that is to say almost −90° to almost +90°). This represents a considerable advantage, particularly in the above-described use in which the patient places a blood glucose meter on a table top.

Another advantage of organic light-emitting diode displays lies in the possible thin and flat construction of the displays. Thus, displays with a total thickness of less than one millimeter can be produced. In this way, it possible for the overall height be reduced, and also the overall volume, which is a considerable advantage for those using portable devices. Moreover, the weight of the portable medical systems can also be reduced in this way, such that the user-friendliness is greatly enhanced. In addition, organic light-emitting diode displays can be produced inexpensively, such that low-cost devices can also be equipped with this technology.

Another advantage is that organic light-emitting diode displays can be used in a much more versatile way than conventional LCDs, in particular passive-matrix LCDs. One point here is that the organic light-emitting diode displays have excellent switch times, that is to say in particular switch times well below one millisecond, even in passive-matrix control, as a result of which such passive-matrix displays are already as such video-capable, thus also allowing the presentation of very rapid image sequences, for example rapidly changing measurement values or animated graphics. In conventional liquid-crystal displays, this is possible only by using additional technologies, in particular using transistor circuits for control (active-matrix circuits). Furthermore, organic light-emitting diode displays in the form of matrix displays can be configured very flexibly and permit flexible presentation of the display content and therefore much better user guidance for the diabetic than is possible by means of a segmented display. This has a positive influence not only for measurement of the blood glucose concentration, but also for other settings, for example setup configurations, and for data management functions, warnings, messages, presentation of (brief) instructions, etc.

Furthermore, in the portable medical system according to the invention, use is made of the fact that OLED displays are driven by current (that is to say the brightness is typically proportional to the current passed through the OLED), whereas typical liquid-crystal displays are voltage-controlled. Accordingly, the proposed portable medical system is provided with a monitoring device. This monitoring device is intended to include a device for detecting at least one drive current through the at least one organic light-emitting diode display. In addition, a device can also be provided for comparing the at least one drive current to at least one predefined setpoint value.

This results in what is called a fail-safe function, in which, for example, current output stages of drive ICs for driving the OLEDs are monitored in order to ascertain whether a current that has been set is actually flowing through. In the event of a deviation between a setpoint value and an actual value, it is in this way possible to conclude that a fault has occurred. It is sometimes even possible to infer the nature of the fault, for example a fault in a specific pixel and/or in a specific row and/or in a specific column. These faults can, for example, be reported back to the portable medical system, for example a central computer.

Furthermore, the monitoring device comprises, for example, at least one warning device for generating a warning for a user, said warning device outputting a warning to a user when the at least one drive current deviates from the at least one predefined setpoint value by more than a predefined amount. In this way, for example, warnings and corresponding instructions can be output on the at least one display element (that is to say for example on the organic light-emitting diode display itself or on a separate display, for example an alert symbol). It is thus possible to prevent a situation where patients work with incorrect measurement values or output values, shown on the at least one display element, and on this basis calculate their medication. For example, a warning can be output to the effect that the portable medical system needs to be serviced and/or should not be used any more. The above-described dangers of a faulty display, with the attendant risk of fatally incorrect medication, are thus almost completely eliminated. This is a crucial advantage particularly in the medical field, where the appliances used have to be absolutely reliable.

The possibility of carrying out a measurement directly at an interface to the actual display, and of accordingly detecting a fault, is greatly simplified by the current-operated function of the organic light-emitting diode display compared to the voltage-controlled liquid-crystal display element. In this connection, particularly in conventional liquid-crystal displays, production tolerances mean that a comparable measurement at an interface to the display can be made only with difficulty.

The embodiments of a portable medical system according to the present invention can also be advantageously developed in various ways. Thus, for example, the at least one organic light-emitting diode display can have at least one flexible display element. This can in particular be a display element with a transparent flexible substrate, in particular a flexible glass and/or plastic substrate. "Flexible" is to be understood here as meaning generally that, in contrast to rigid displays, at least a slight bending can be effected by manual application of a force. For example, the organic light-emitting diode display can be equipped with a flexible transparent plastic or glass substrate, it being possible, for example, to use glass substrates with a thickness of less than 200 µm in one embodiment, and of less than 100 µm in other embodiments.

This development of the present invention not only has the advantage that the entire portable medical system and in particular the at least one display element are flexible and can therefore be adapted to the environment. The flexibility of the at least one display element is also of considerable advantage in terms of reliability. This is due in particular to the fact that flexible displays are able to withstand considerably greater mechanical shocks than conventional rigid displays. In the case of portable glucose meters or portable insulin pumps in particular, it may happen that the medical system is dropped by the patient (particularly by elderly patients), which in many cases results in the display element being destroyed. In the case of flexible display elements, however, the risk of breakage is greatly reduced. Here too, the use of OLEDs again has a positive effect, since OLEDs can be made much more flexible than liquid-crystal displays, in which a liquid is enclosed between two transparent substrates.

In another advantageous embodiment of the portable medical system of the present invention, an optimization device is used. This optimization device is intended to comprise at least one brightness sensor for detecting the brightness of the ambient light and furthermore to comprise a device for automatic adjustment, in particular optimization, of brightness and/or contrast and/or power consumption of the at least one display element, in particular of the at least one organic light-emitting diode display. This development of the invention affords the possibility of adjusting the display brightness of the at least one display element as a function of the ambient light in such a way that, in all ambient lighting conditions, there is always optimal brightness (in particular no glare in the dark), high contrast and minimal power consumption. This is another important advantage of using organic light-emitting diode displays compared to liquid-crystal displays since, as has been described above, contrast and brightness cannot generally be optimized simultaneously in liquid-crystal displays.

The use of the optimization device is of particular advantage especially in the medication of diabetic patients. As has been described above, this is partly because patients suffering from diabetes often have impaired visual acuity. It is therefore of particular importance here to optimize the display elements in terms of contrast and/or brightness.

The use of OLED displays according to the invention is also possible without the above-described monitoring device, but with an optimization device being provided. A portable medical system is accordingly proposed, in particular for the purposes of analysis and/or medication, comprising at least one medical monitoring device and/or analysis device and/or medication device and furthermore comprising at least one display element. The at least one display element comprises at least one organic light-emitting diode display. Furthermore, an optimization device is provided which comprises at least one brightness sensor for detecting the brightness of the ambient light. Furthermore, the optimization device comprises a device for automatic adjustment, in particular optimization, of at least one of the following parameters of the at least one display element: brightness, contrast, power consumption. This proposed portable medical system can additionally and optionally be embodied in accordance with the above-described developments.

Furthermore, the use of OLED displays is particularly advantageous in insulin pumps or other medication pumps. This is mainly due to the fact that such insulin pumps are often worn on a belt or under clothing on the body, for example in the waist region. This means that these systems may involve particularly wide reading angles, since the patient will only rarely remove the insulin pump from the body in order to read it and will instead attempt to read the display at a viewing direction almost parallel to the display surface.

A medication control system is therefore also specifically proposed that has at least one display element. The at least one display element comprises at least one organic light-emitting diode display. This medication control system is designed to regulate or control at least one medication, i.e. the dosing of a physiologically active substance. The medication control system can thus comprise an insulin pump, for example. Alternatively or in addition, the medication control system can also comprise an artificial pancreas, that is to say a control system having a blood glucose measurement system and a regulated micropump for dosing insulin according to the measured blood glucose value. Other types of medication systems that permit a measurement and a corresponding dosing of a substance can be included by analogy under this term and are intended to be covered by the scope of protection of the invention. Thus, the medication control system can alternatively or additionally comprise a continuous monitoring system, that is to say a system that records physiological data (e.g. a blood glucose value or the like) continuously (for example by means of an implanted sensor) and delivers a medication accordingly. A design of the medication control system as purely a monitoring system, i.e. as a system with only a measurement function and without direct initiation of medication and/or control, is also conceivable and is intended to be covered by the term "medication control system,".

In contrast to certain prior art disclosures which simply propose that the data obtained with the device be used for medication, a medication control system according to the invention is equipped directly with an organic light-emitting diode display. In contrast to the portable medical systems described above, however, the medication control system does not necessarily have to be provided with a monitoring device or an optimization device. Nevertheless, the advantageous embodiments described above can also be provided analogously.

In addition to the portable medical systems according to the invention and the insulin pump according to the invention in one of the described embodiments, the invention further proposes the use of an organic light-emitting diode display as display element in a portable medical system according to the above description. Here, organic light-emitting diode displays according to one of the illustrative embodiments described above and the advantageous developments of the portable medical system can be used individually or in combination.

Further details and features of the present invention will become clear from the following detailed description of an illustrative embodiment in which the respective features can be embodied either singly or in several combinations with one another to form various other embodiments. The scope of the present invention is not limited to the particular illustrative embodiment.

BRIEF DESCRIPTION OF THE DRAWINGS

The following detailed description of the embodiments of the present invention can be best understood when read in conjunction with the following drawing, where like structure is indicated with like reference numerals and in which:

FIG. 1 shows a schematic view of an illustrative embodiment of a portable medical system with an organic light-emitting diode display.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

An illustrative embodiment of a portable medical system 110 according to the invention is shown in FIG. 1. In this illustrative embodiment, the portable medical system 110 has a blood glucose meter 112 which, by means of a test strip 114, can determine electro-chemically the blood glucose content in a blood droplet 116. As has been described above, an insulin pump can also be used according to the invention instead of a blood glucose meter 112.

The blood glucose meter 112 comprises an insert slit 118 into which the test strip 114 equipped with corresponding electrodes 120 can be inserted. The test strip 114 can be equipped, for example, like test strips known from the prior art, for example the test strips known from U.S. Pat. No. 5,286,362. When the test strip 114 is inserted into the insert slit 118, the electrodes 120 of the test strip 114 are contacted by evaluation and measurement electronics 122, and an electrochemical determination of the analyte concentration in the blood droplet 116 is carried out.

The evaluation and measurement electronics 122 are connected to a central processor unit 124 which controls the measurement by the evaluation and measurement electronics 122 and evaluates measurement results. The central processor unit 124 can additionally include various memories, and other data memories (not shown) can be provided, in particular memories with a database function. In this way, the measurements carried out by the evaluation and measurement electronics 122 are not only evaluated, but also correspondingly stored and displayed, such that they are at all times available to a patient. For example, a user can exploit the functions of the central processor unit 124 via control elements 125 and thus carry out a measurement or can also display measurement results that have been stored earlier. Such functions of blood glucose meters 112 are known from the prior art.

Furthermore, the portable medical system 110 shown in FIG. 1 has a display element 126. In this illustrative embodiment, this display element 126 comprises an OLED passive-matrix display 128, for example a monochrome or color VGA display, that is to say a display with a resolution of 640×480 pixels, or other, for example smaller, displays. By suitable control of these pixels, alphanumeric pictures, graphs, symbols or even video images can be presented on the OLED passive-matrix display 128. Alternatively or in addition, one or more OLED active-matrix displays could also be used.

Furthermore, the display element 126 comprises a symbol bar 130 with individual light-emitting symbols, for example a segmented battery status display, a warning symbol or a database symbol. This symbol bar can, for example, again comprise organic light-emitting diodes, or other types of display elements or illuminations can also be provided, for example illuminations with inorganic light-emitting diodes. In this way, it is possible to ensure that the symbol bar 130 functions independently of the mode of function of the OLED passive-matrix display 128 and is also ready for use if the latter fails.

The display element 126 is controlled by a drive unit 132, which can in turn be composed of individual subunits (not shown). Thus, for example, different drives can be provided for the OLED passive-matrix display 128 and for the symbol bar 130 with its individual symbols. The individual component parts 128, 130 of the display element 126 are supplied with corresponding drive signals via drive lines 134, 136, 138, for example liquid-crystal display elements are supplied with suitable voltages or OLED display elements with suitable currents. In this illustrative embodiment, a drive line 134 for columns and a drive line 136 for rows are provided for the OLED passive-matrix display 128. Other configurations are also conceivable. In particular, an active-matrix display can also be used instead of a passive-matrix display.

The drive unit 132 and the number and configuration of the drive lines 134, 136, 138 must accordingly be adapted to the actual circumstances. An energy supply, which can be present in the form of batteries or accumulators, for example, and which accordingly supplies the central processor unit 124 and the drive unit 132 with energy, is not shown in FIG. 1.

Furthermore, the display element 126 in the illustrative embodiment according to FIG. 1 has an optimization device 141 with a brightness sensor 140 which, for example, can include a photodiode. This brightness sensor is advantageously integrated on a common surface of the display element 126, such that the distance to the OLED passive-matrix display 128 is as small as possible. Individual pixels in the OLED passive-matrix display 128 can even be left out and replaced by corresponding photosensors.

The brightness sensor 140 is in turn connected to the drive unit 132. Alternatively or in addition, a connection to the central processor unit 124 can also be provided. Additional electronic components for evaluation of the brightness sensor 140 can also be provided.

A device 142 which is used for automatic adjustment of the display element 126, and which is also a component part of the optimization device 141, is also provided, in this case in the drive unit 132 (alternatively or additionally also in the central processor unit 124). This device 142 for automatic adjustment of the display element evaluates the signals from the brightness sensor 140 and automatically optimizes the mode of function of the drive unit 132 such that the OLED passive-matrix display 128 works with optimal contrast, adapted to the brightness conditions, and with optimal brightness, and at the same time with minimal power consumption. The brightness of the symbol bar 130 (or of the individual symbols) can also be correspondingly optimized. However, such optimization does not necessarily mean that the luminance of the OLED passive-matrix display 128 is reduced under "good" ambient lighting conditions (that is to say in bright surroundings) and increased under "poor" ambient lighting conditions. Rather, the adaptation of the eye to dark ambient lighting conditions often means that lower luminance levels are sufficient when working in dark environments. When working with OLED passive-matrix displays 128 in bright environments, on the other hand, a negative effect is that the ambient light is often reflected off electrodes of the OLED passive-matrix display 128, which reduces the contrast and therefore often requires higher luminance levels to maintain readability. All of this can be included in an optimization.

Furthermore, in the embodiment shown in FIG. 1, the drive unit 132 of the blood glucose meter 112 comprises a monitoring device 144 for monitoring the function of the display element 126. This monitoring device 144 is composed of a current-detecting device 146 and of a comparison device 148. The current-detecting device 146 measures (continuously or at defined time intervals) the drive current or several drive currents, which flow from the drive unit 132 to the OLED passive-matrix display 128 and/or to the symbol bar 130.

Currents running through the individual drive lines 134, 136, 138 can be detected separately, and it is even possible for currents running through individual rows or columns of the OLED passive-matrix display 128 to be detected separately. The comparison device 148 evaluates the results of the current-detecting device 146 and compares the measured currents to predefined setpoint values. For example, these can be setpoint values that are stored in a data memory, for example a data memory (not shown) of the central processor unit 124. These setpoint values can be variably adapted during the operation of the display element 126. For example, the setpoint values can be adapted to the optimal currents predefined by the device 142 for automatic adjustment of the display element, such that the setpoint values are dependent on the surrounding brightness. Other configurations are also possible.

In addition to setpoint values, tolerance thresholds can also be predefined. For example, it is possible for the system to be predefined such that a fault is detected if certain values are not reached, for example a deviation from the predefined setpoint values by more than a predefined amount, of if additional predefined thresholds are exceeded or not reached. In this case, the monitoring device 144 can, for example, deliver a corresponding error message to the central processor unit 124, if appropriate even an error message specifying the exact nature of the fault. The central processor unit 124 can then cause a corresponding warning to be output to a person using the blood glucose meter 112. This can be an acoustic warning, for example, or can also involve the activation of corresponding warning symbols or warning messages, for example a warning symbol in the symbol bar 130. The corresponding faults can also be stored in the central processor unit 124 or in separate data memories and can then be read out for diagnostic purposes by a service engineer when servicing the blood glucose meter 112. In addition to the display element 126, separate display elements can also be provided, for example a display element that only shows the warning text to the effect that the blood glucose meter 112 needs to be serviced and should not be used any more.

An advantageous development of the portable medical system 110 will also be explained on the basis of FIG. 1. Thus, it is possible to equip the portable medical system 110 with a solar cell. This solar cell can be arranged, for example, on a user surface of the portable medical system 110, for example alongside the display element 126, or also as a component part of the display element 126. This solar cell can be used to at least partially supply the portable medical system with electrical energy. In addition, further energy stores can be used, for example batteries and/or accumulators. It is also conceivable for these additional energy stores to be charged via the energy supplied from the at least one solar cell.

In one particular embodiment, this at least one solar cell, as shown in FIG. 1, is at least partially identical in terms of component parts to the brightness sensor 140. Thus, this brightness sensor 140 can advantageously be replaced entirely by a corresponding solar cell. The portable medical system 110 is then advantageously designed in such a way that the brightness and/or the contrast of the display element 126 is adjusted as a function of the electrical energy provided by the at least one solar cell, for example as a function of a solar current. This can be achieved, for example, if, in the event of strong sunlight, the current additionally supplied by the solar cell is utilized to operate the display element 126, in particular the OLED display 128, with greater luminance. In this way, for example, the readability of the OLED display 128 is increased in direct sunlight. In this case, the solar cell forms part of the optimization device 141, which automatically adjusts the brightness and/or contrast of the display element 126. In this case, it is possible to dispense with a complicated additional control of the display brightness or contrast, or the outlay for such electronics can be considerably reduced, since the "measurement" signal of the sunlight can be integrated directly into the parameter of the drive current for the display element 126.

The customary solar cell systems known from solar technology can in principle be used for the solar cell. For example, inorganic solar cells with at least one inorganic semiconductor material can be used. However, it is also possible, alternatively or in addition, for the solar cell to include an organic solar cell, that is to say a solar cell with at least one organic semiconductor material. For example, it is possible to use solar cells with polymers or low molecular organic materials as organic semiconductor, or also hybrid elements with both organic and also inorganic components. Organic solar cells of this kind, for example using conjugated polymers, are known for example from the works of A. Heeger et al, for which the Nobel prize for chemistry was awarded in the year 2000. The use of organic solar cells in combination with the OLED display 128 affords, in particular, the technically interesting advantage of being able to use display elements 126 that comprise organic brightness sensors 140 in the form of organic solar cells, and also the OLED displays 128 and if appropriate the symbol bar 130, which can be produced entirely using organic semiconductor technology (all organic devices). In this case, the use of expensive inorganic semiconductor technology could be dispensed with entirely.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A portable medical system configured for purposes of at least one of analysis and medication and having one or more of a medical monitoring device, analysis device and medication device, the system comprising at least one display element comprising at least one organic light-emitting diode display, and further comprising a processor including a memory and at least one predefined setpoint value stored in the memory, at least one brightness sensor configured for detecting the brightness of the ambient light, wherein the processor is configured to variably adapt the at least one predefined setpoint value in response to the brightness of the ambient light during operation of the at least one organic light-emitting diode display, a monitoring device configured for detecting at least one drive current of the at least one organic light-emitting diode display, a comparison device configured for comparing the at least one drive current to the at least one predefined setpoint value, the monitoring device further having at least one warning device configured for generating a warning for a user when a measured value of the at least one drive current deviates from the at least one predefined setpoint value by more than a predefined amount.

2. The portable medical system of claim 1 comprising at least one analysis system configured for detecting at least one analyte in a liquid sample.

3. The portable medical system of claim 2 wherein the analysis system is configured for detecting at least one of blood glucose, cholesterol and coagulation.

4. The portable medical system of claim 2 wherein the analysis system is configured for detecting the analyte by means of at least one reagent.

5. The portable medical system of claim 1 comprising a medication device comprising at least one medication pump.

6. The portable medical system of claim 5 wherein the medication pump comprises an insulin pump.

7. The portable medical system of claim 1 wherein the at least one organic light-emitting diode display comprises at least one matrix display.

8. The portable medical system of claim 7 wherein the matrix display comprises an organic passive-matrix display.

9. The portable medical system of claim 1 wherein the at least one organic light-emitting diode display comprises at least one flexible display element having a transparent flexible substrate.

10. The portable medical system of claim 9 wherein the transparent flexible substrate comprises glass or plastic.

11. The portable medical system of claim 1 further comprising an optimization device comprising the at least one brightness sensor configured for detecting the brightness of the ambient light, and further comprising an adjustment device configured for automatic adjustment of at least one parameter of the at least one display element, the at least one parameter being selected from the group consisting of: brightness, contrast, and power consumption.

12. The portable medical system of claim 11 further comprising at least one solar cell configured for at least partially supplying the portable medical system with electrical energy.

13. The portable medical system of claim 12 wherein the at least one solar cell and the at least one brightness sensor each comprise structural parts that are at least partially identical to each other.

14. The portable medical system of claim 12 wherein the portable medical system is configured to adjust at least one of brightness and contrast of the at least one display element as a function of an electrical current generated from the electrical energy provided by the at least one solar cell.

15. The portable medical system of claim 1 further comprising at least one solar cell configured for at least partially supplying the portable medical system with electrical energy.

16. The portable medical system of claim 15 wherein the solar cell comprises one of an inorganic solar cell with at least one inorganic semiconductor material and an organic solar cell with at least one organic semiconductor material.

17. The portable medical system of claim 1, wherein the at least one warning device is configured for generating the warning for the user when the at least one drive current actually flowing through the at least one organic light-emitting diode display is measured and deviates by more than the predefined amount from the at least one predefined setpoint, wherein the at least one predefined setpoint is a predefined drive current value adapted to drive a non-faulty organic light-emitting diode display.

\* \* \* \* \*